United States Patent
Holmberg et al.

(10) Patent No.: US 10,370,382 B2
(45) Date of Patent: Aug. 6, 2019

(54) PROCESS FOR PREPARING HYDROMORPHONE AND DERIVATIVES THEREOF

(71) Applicant: Cambrex Charles City, Inc., Charles City, IA (US)

(72) Inventors: Pär Holmberg, Charles City, IA (US); Michael Robert Tracey, Charles City, IA (US); Zhiming Eric Dong, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 0 days.

(21) Appl. No.: 15/747,980

(22) PCT Filed: Jul. 26, 2016

(86) PCT No.: PCT/GB2016/052285
§ 371 (c)(1),
(2) Date: Jan. 26, 2018

(87) PCT Pub. No.: WO2017/017436
PCT Pub. Date: Feb. 2, 2017

(65) Prior Publication Data
US 2018/0354961 A1 Dec. 13, 2018

(30) Foreign Application Priority Data

Jul. 27, 2015 (GB) .................................. 1513203.8

(51) Int. Cl.
*C07D 489/04* (2006.01)
*A61K 31/485* (2006.01)
*C07D 489/02* (2006.01)

(52) U.S. Cl.
CPC ......... *C07D 489/04* (2013.01); *C07D 489/02* (2013.01)

(58) Field of Classification Search
CPC ... C07D 489/04; C07D 489/02; A61K 31/485
USPC ........................................... 546/45; 514/282
See application file for complete search history.

(56) References Cited

U.S. PATENT DOCUMENTS

| | | | |
|---|---|---|---|
| 2,649,454 A | 8/1953 | Rapoport | |
| 4,673,679 A * | 6/1987 | Aungst | A61K 9/006 514/282 |
| 5,071,985 A | 12/1991 | Andre et al. | |
| 7,674,800 B2 | 3/2010 | Chapman et al. | |
| 7,851,482 B2 | 12/2010 | Dung et al. | |
| 8,252,808 B2 * | 8/2012 | Wang | C07D 489/04 514/289 |
| 8,399,671 B2 | 3/2013 | Orr et al. | |
| 8,461,137 B2 | 6/2013 | Mickle et al. | |
| 2004/0213828 A1 | 10/2004 | Smith | |
| 2006/0009479 A1 | 1/2006 | Bailey et al. | |
| 2009/0156818 A1 | 6/2009 | Wang et al. | |

FOREIGN PATENT DOCUMENTS

| | | |
|---|---|---|
| CN | 103113378 A | 5/2013 |
| DE | 607931 C | 1/1935 |
| DE | 617238 C | 10/1935 |
| DE | 623821 C | 1/1936 |
| EP | 0359647 A1 | 3/1990 |
| WO | 2008070658 A1 | 6/2008 |
| WO | 2012003468 A1 | 1/2012 |

OTHER PUBLICATIONS

International Search Report From PCT/GB2016/052285 dated Dec. 19, 2016.
Yajima, Haruaki, et al., "Trifluoromethanesulphonic Acid, as a Deprotecting Reagent in Peptide Chemistry." J. Chem. Soc., Chem. Comm. (1974), Received Sep. 24, 1973, pp. 107-108.
Andre, Jean-Daniel, "O'Demethylation of Opioid Derivatives Wtih Methane Sulfonic Acid / Methionine : Application to the Synthesis of Naloxone and Analogues." Synthetic Communications, vol. 22, No. 16, Received in UK Apr. 8, 1992, pp. 2313-2327.
Fujii N, Irie H, Yajima H. Regioselective cleavage of aromatic methyl ethers by methanesulphonic acid in the presence of methionine. Journal of the Chemical Society, Perkin Transactions 1. Jan. 1, 1977(20):2288-9.
Carroll RJ, Leisch H, Rochon L, Hudlicky T, Cox DP. One-pot conversion of thebaine to hydrocodone and synthesis of neopinone ketal. The Journal of organic chemistry. Dec. 11, 2008;74(2):747-52.

\* cited by examiner

*Primary Examiner* — Charanjit Aulakh
(74) *Attorney, Agent, or Firm* — Lerner, David, Littenberg, Krumholz & Mentlik, LLP

(57) ABSTRACT

There is provided a novel process for the preparation of a compound of formula (I), wherein R¹ is as described in the description, by demethylation of a corresponding O-methyl derivative.

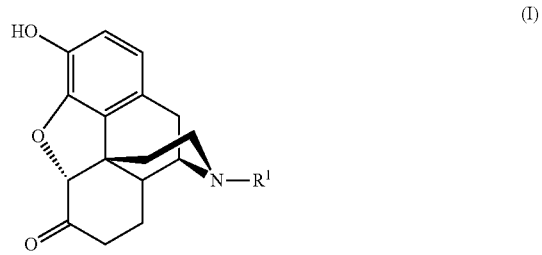

23 Claims, No Drawings

PROCESS FOR PREPARING HYDROMORPHONE AND DERIVATIVES THEREOF

CROSS-REFERENCE TO RELATED APPLICATIONS

This application is a national phase entry under 35 U.S.C. § 371 of International Application No. PCT/GB2016/052285, filed Jul. 26, 2016, which claims priority to GB 1513203.8, filed Jul. 27, 2015, the disclosures of which are incorporated herein by reference.

FIELD OF THE INVENTION

The present invention relates to a new demethylation process that is useful in the synthesis of certain semi synthetic opioids/alkaloids (including opioid receptor agonists, antagonists and other derivatives thereof) and/or intermediates thereto. In particular, the invention relates to new processes for modifying semi synthetic opioids/alkaloids that are structurally related to morphine.

BACKGROUND OF THE INVENTION

Several semi synthetic opioids are structurally related in that they only differ by virtue of the presence of a methoxy substituent, instead of a hydroxy substituent, on the aromatic ring of the phenanthrene. Such structurally related opiate compounds with a morphinan core include morphinone, codeinone, 14-hydroxymorphinone, 14-hydroxycodeinone, oxymorphone, oxycodone, hydromorphone and hydrocodone. These compounds can be prepared from starting materials such as morphine, codeine, oripavine and thebaine, or even from each other.

Traditionally, hydrocodone and hydromorphone have been synthesized in a two-step sequence from codeine and morphine: hydrogenation followed by an Oppenauer oxidation. The process is cumbersome and, for hydromorphone, low yielding. More recently hydrocodone and hydromorphone have been prepared from thebaine and oripavine respectively in a two-step sequence which includes a selective hydrogenation followed by hydrolysis of the resulting enol ether.

It is desirable to reduce the amount of the α,β-unsaturated ketone derivative (e.g. codeinone, morphinone) that is present in the final product, due to potentially adverse toxicological properties that can be associated with such derivatives. International patent applications nos. WO 2012/003468 and WO 2008/070658 and U.S. Pat. Nos. 7,674,800 and 7,851,482 disclose processes for producing opiates, such as oxymorphone, containing reduced amounts of the enone derivatives. However, these documents do not disclose the demethylation of opioids which contain a methoxy group.

H. Yajima, et al., *J. Chem. Soc., Chem. Comm.*, 1974, 107, discusses the use of trifluoromethanesulfonic acid as a deprotecting reagent in peptide chemistry. However, there is no discussion of the need to avoid forming unwanted impurities, such as α,β-unsaturated ketone derivatives. It is important to minimise the formation of such impurities in these processes, particularly when the processes are involved in the formation of pharmaceutical substances for administration to patients.

U.S. Pat. No. 5,071,985 and J. D. Andre, et al., *Synth. Comm.*, 22(16), 2313-2327 (1992) disclose processes for demethylating certain morphinan derivatives. However, there is no discussion of the need to minimise the formation of unwanted impurities, particularly α,β-unsaturated ketone derivatives.

The present invention addresses some of the problems associated with the processes of the prior art.

The listing or discussion of an apparently prior-published document in this specification should not necessarily be taken as an acknowledgement that the document is part of the state of the art or common general knowledge.

DISCLOSURE OF THE INVENTION

According to a first aspect of the present invention, there is provided a process for the preparation of a compound of formula I,

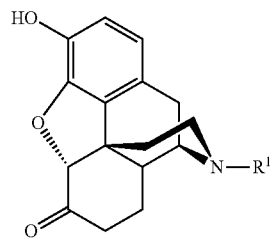

or a pharmaceutically acceptable salt thereof;
wherein:
$R^1$ represents hydrogen or $C_{1-12}$ alkyl, $C_{2-12}$ alkenyl, $C_{2-12}$ alkynyl or $C_{3-12}$ cycloalkyl, (which latter four groups are optionally substituted by one or more halogen atoms or phenyl groups);
which process comprises contacting a compound of formula II,

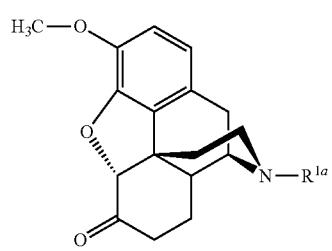

or a salt thereof, wherein $R^{1a}$ is defined according to $R^1$, with a mixture comprising water, a carboxylic acid, a sulfonic acid, and a sulfide compound;
wherein the sulfide compound is selected from the group consisting of cyclic sulfur-containing compounds and sulfides of formula III, $$X^1-S-X^2 \qquad \qquad III$$

wherein $X^1$ and $X^2$ each independently represents hydrogen, phenyl, $-C(O)R^3$ or a $C_{1-12}$ alkyl group (optionally substituted by one or more groups selected from halogen, $-OH$, $-NH_2$, phenyl, $-O-C_{1-4}$ alkyl, $-C(O)R^4$ and $-S(O)_m-C_{1-4}$ alkyl);
$R^3$ and $R^4$ independently represent $-OH$, $-C_{1-4}$ alkyl or $-O-C_{1-4}$ alkyl; and m represents from 0 to 2;
which process is hereinafter referred to as "the process of the invention".

The process of the invention may be performed employing salts or solvates (of compounds of formula II), and may produce compounds that are in the form of a (e.g. corresponding) salt or solvate (of compounds of formula I). Particular salts that may be mentioned include organic acid salts such as tartrate salts (e.g. bitartrate salts) and inorganic acid salts such as hydrohalide salts (e.g. hydrochloride salts). However, in certain embodiments of the invention, the process of the invention is performed using the free base of the compound of formula II.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Unless otherwise specified, alkyl groups, alkenyl groups and alkynyl groups as defined herein may be straight-chain or, when there is a sufficient number (i.e. a minimum of three) of carbon atoms be branched-chain. Cycloalkyl groups may be fully or partly cyclic (for example a $C_4$ cycloalkyl group may be a —$CH_2$-cyclopropyl group).

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

The term "aryl", when used herein, includes $C_{6-10}$ aryl groups. Such groups may be monocyclic or bicyclic and, when polycyclic, be either wholly or partly aromatic. $C_{6-10}$ aryl groups that may be mentioned include phenyl, naphthyl, indenyl, and the like. For the avoidance of doubt, the point of attachment of substituents on aryl groups may be via any carbon atom of the ring system.

Unless otherwise specified, the term "heteroaryl" or "heteroaromatic" when used herein refers to an aromatic group containing one or more heteroatom(s) (e.g. one to four heteroatoms) preferably selected from N, O and S. Heteroaryl groups include those which have from 5 to 10 members (e.g. from 5 to 7) and may be monocyclic or bicyclic, provided that at least one of the rings is aromatic (so forming, for example, a mono- or bicyclic heteroaromatic group). When the heteroaryl group is polycyclic the point of attachment may be via any atom including an atom of a non-aromatic ring. However, when heteroaryl groups are polycyclic (i.e. bicyclic), they are preferably linked to the rest of the molecule via an aromatic ring. Heteroaryl groups that may be mentioned include benzofuranyl, furanyl, imidazolyl, indolyl, isoquinolinyl, oxazolyl, pyrazinyl, pyrazolyl, pyridazinyl, pyridyl, pyrimidinyl, pyrrolyl, quinolinyl, tetrahydroquinolinyl, thiazolyl and thienyl. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom). Heteroaryl groups may also be in the N- or S-oxidised form.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is from 3 to 10 (e.g. from 5 to 8). Further, such heterocycloalkyl groups may be saturated or unsaturated containing one or more double and/or triple bonds, forming for example a $C_{2-q}$ heterocycloalkenyl (where q is the upper limit of the range) group. Heterocycloalkyl groups that may be mentioned include azetidinyldioxolanyl, dioxanyl, imidazolidinyl, morpholinyl, piperazinyl, piperidinyl, non-aromatic pyranyl, pyrazolidinyl, pyrrolidinyl, and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom). Heterocycloalkyl groups may also be in the N- or S-oxidised form.

For the avoidance of doubt, the term "bicyclic" (e.g. when employed in the context of heterocycloalkyl groups) refers to groups in which the second ring of a two-ring system is formed between two adjacent atoms of the first ring.

The terms "halo", "halogen" and "halide", when used herein, include fluoro, chloro, bromo and iodo.

The term "about" as used herein, when referring to a measurable value (such as an amount of a particular component in the reaction mixture), refers to variations of ±20%, ±10%, ±5%, ±1%, ±0.5%, or ±0.1% of the specified amount.

In particular embodiments of the invention, $R^1$ in the compound of formula I represents hydrogen, $C_{1-6}$ alkyl, $C_{2-6}$ alkenyl, $C_{2-6}$ alkynyl or $C_{3-6}$ cycloalkyl, (which latter four groups are optionally substituted by one or more halo atoms or phenyl groups). In other particular embodiments, $R^1$ represents hydrogen, $C_{1-6}$ alkyl or $C_{3-6}$ cycloalkyl (which latter two groups are optionally substituted by one or more phenyl groups). In further particular embodiments, $R^1$ represents methyl, ethyl, propyl, butyl, benzyl, —$CH_2$-cyclopropyl, or $CH_2$—CH=$CH_2$. In still further particular embodiments, $R^1$ represents methyl, ethyl, propyl, butyl, benzyl, or —$CH_2$-cyclopropyl. In preferred embodiments, $R^1$ represents methyl.

A particular compound of formula I that may be mentioned in this respect is hydromorphone:

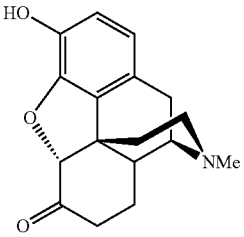

which may be prepared by demethylation of an appropriate compound of formula II according to the conditions described herein.

The processes of the invention involve contacting a compound of formula I, or a salt thereof, with a mixture comprising water, a carboxylic acid, a sulfonic acid, and a sulfide compound. The components of said mixture may be added in any order.

The process of the present invention is conducted in the presence of water. By this, we mean that the reaction is conducted in a medium which contains additional water (i.e. an amount of water that is greater than the amount that is normally present in the other reaction components (particularly the carboxylic acid and sulfonic acid) when these are obtained from conventional sources (i.e. "laboratory grade" reagents)). For example, the process of the invention may include the step of adding water to the compound of formula II. This water may be added before or after the compound of formula II is brought into contact with the acidic components, or it may be added to the acidic components before they are brought into contact with the compound of formula II.

In a preferred embodiment of the invention, the water is deionised water or purified water.

In an embodiment of the invention, the amount of water that is present in the reaction mixture may be at least about 0.1% (e.g. at least about 1%) by weight relative to the combined weight of the water and the compound of formula II. For example, the amount of water that is present in the reaction mixture may be from about 0.1% to about 70% (e.g. from about 1% to about 60%) by weight relative to the combined weight of the water and the compound of formula II. For example, a reaction mixture containing equal masses of water and compound of formula II would have a water quantity of 50% by weight relative to the combined weight of the water and the compound of formula II. In particular embodiments, the amount of water that is present in the reaction mixture may be from about 2% to about 50%, from about 5% to about 30%, or from about 10% to about 20% by weight relative to combined weight of the water and the compound of formula II.

The process of the invention is performed in the presence of a sulfide compound. The sulfide compound is a compound selected from the group consisting of:
(i) a cyclic sulfur-containing compound; and
(ii) a sulfide of formula III,

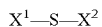

wherein $X^1$ and $X^2$ each independently represents hydrogen, phenyl, —C(O)R$^3$ or a $C_{1-12}$ alkyl group (optionally substituted by one or more groups selected from halogen, —OH, —NH$_2$, phenyl, —O—C$_{1-4}$ alkyl, —C(O)R$^4$ and —S(O)$_m$—C$_{1-4}$ alkyl);

$R^3$ and $R^4$ independently represent —OH, —C$_{1-4}$ alkyl or —O—C$_{1-4}$ alkyl; and m represents from 0 to 2.

By the use of the term "cyclic sulfur-containing compound" we mean a heterocyclic compound in which at least one of the heteroatoms within the ring is a sulfur atom. Said heterocyclic compound may be formed from a heteroaromatic or heterocycloalkyl ring, provided that at least one of the heteroatoms within the ring is a sulfur atom.

Particular examples of such heterocyclic compounds include:
(i) a monocyclic aromatic compound containing one or more sulfur atoms within the aromatic ring; and
(ii) a compound of formula IV

wherein n represents from 0 to 3.

Thus, in a particular embodiment of the invention, the sulfide compound is:
(a) a monocyclic aromatic compound containing one or more sulfur atoms within the aromatic ring;
(b) a compound of formula IV

wherein n represents from 0 to 3; or (c) a sulfide of formula III,

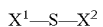

wherein $X^1$ and $X^2$ each independently represents hydrogen, phenyl, —C(O)R$^3$ or a $C_{1-12}$ alkyl group (optionally substituted by one or more groups selected from halogen, —NH$_2$, phenyl, —C(O)R$^4$ and —S(O)$_m$—C$_{1-4}$ alkyl);

$R^3$ and $R^4$ independently represent —OH, —C$_{1-4}$ alkyl or —O—C$_{1-4}$ alkyl; and m represents from 0 to 2.

Particular cyclic sulfur-containing compounds that may be mentioned include cyclohexene sulfide, and, particularly, thiophene, trimethylene sulfide, tetrahydrothiophene and pentamethylene sulfide.

Particular examples of sulfides of formula III include those in which $X^1$ and $X^2$ each independently represents hydrogen, phenyl, —C(O)R$^3$ or a $C_{1-12}$ alkyl group (optionally substituted by one or more groups selected from halogen, —NH$_2$, phenyl, —C(O)R$^4$ and —S(O)$_m$—C$_{1-4}$ alkyl). Other particular examples of sulfides of formula III include those in which $X^1$ and $X^2$ each independently represents a $C_{1-12}$ alkyl group optionally substituted by one or more groups selected from halogen, —C(O)R$^4$ and —S(O)$_m$—C$_{1-4}$ alkyl.

Particular sulfides of formula III that may be mentioned include methionine, tert-butyl methyl sulfide, cyclohexene sulfide, S-phenyl thioacetate, bis(methylthio)methane, methyl (methylsulfinyl)methyl sulfide, di-tert-butyl sulfide, or, preferably, butyl ethyl sulfide, butyl methyl sulfide, dibenzyl sulfide, dibutyl sulfide, diethyl sulfide, diisobutyl sulfide, diisopropyl sulfide, dimethyl sulfide, dioctyl sulfide, diphenyl sulfide, dipropyl sulfide, di-sec-butyl sulfide, dodecyl methyl sulfide, ethyl isopropyl sulfide, ethyl propyl sulfide, isopropyl methyl sulfide, isopropyl propyl sulfide, methyl (methylthio)acetate, pentamethylene sulfide, phenyl trifluoromethyl sulfide, tetrahydrothiophene, thioacetic acid, thioanisole, 2,2'-thiodiacetic acid, thiophene, 3,3'-thiodipropionic acid and trimethylene sulfide.

In more particular embodiments, the sulfide compound is selected from the group consisting of dioctyl sulfide, dipropyl sulfide, diethyl sulfide, dimethyl sulfide, dodecyl methyl sulfide, and, most particularly, dibutyl sulfide.

For the avoidance of doubt, mixtures of two or more of said sulfide compounds may be used in the processes described herein. However, in particular embodiments of the invention, only one sulfide compound is present.

The amount of the sulfide compound should be sufficient to enable the reaction to proceed.

In particular embodiments, the amount of sulfide compound that is present in the reaction is at least about 1 equivalent (i.e. molar equivalent), and preferably at least about 2 equivalents, relative to the compound of formula II. In the most particular embodiments, the amount of sulfide compound that is present in the reaction is from 1 to 6 equivalents (e.g. from 2 to 4 equivalents) relative to the compound of formula II.

The sulfide compound may be added to the reaction at any time. In particular embodiments, the compound of formula II is brought into contact with the carboxylic acid (and optionally the compound of formula II is also brought into contact with the sulfonic acid) before the compound of formula II is brought into contact with the sulfide compound.

It is stated herein that the process of the invention is also performed in the presence of a sulfonic acid. The sulfonic acid is any compound that contains a —S(O)₂OH functional group. For example, the sulfonic acid may be a compound of formula V,

   V wherein R⁵ represents a $C_{1-6}$ alkyl group (optionally substituted by one or more halogen atoms) or an aryl group (optionally substituted by one or more substituents selected from a $C_{1-4}$ alkyl group and a halogen atom).

In particular embodiments, the sulfonic acid is a compound of formula V as defined above, wherein R⁵ represents a $C_{1-3}$ alkyl group (optionally substituted by one or more halogen atoms) or a phenyl group (optionally substituted by one or more substituents selected from a methyl group and a halogen atom). Particular sulfonic acids that may be mentioned include methane sulfonic acid, trifluoromethane sulfonic acid and toluenesulfonic acid. For the avoidance of doubt, mixtures of two or more of said sulfonic acids may be used in the processes described herein. For example, in particular embodiments, the sulfonic acid that is used in the process of the invention may be a mixture of methane sulfonic acid and toluenesulfonic acid.

The amount of the sulfonic acid should be sufficient to enable the reaction to proceed. In particular embodiments, the amount of the sulfonic acid that is present in the reaction is from about 1 to about 10 equivalents (i.e. molar equivalents), such as from about 2 to about 8 equivalents, relative to the compound of formula II. In embodiments in which trifluoromethane sulfonic acid is the principal (e.g. sole) sulfonic acid present, the amount of sulfonic acid that is present in the reaction may be from about 1 to about 3 equivalents relative to the compound of formula II. In the most particular embodiments (for example, embodiments in which methane sulfonic acid is the principal (e.g. sole) sulfonic acid present), the amount of sulfonic acid that is present in the reaction may be from about 5 to about 7 equivalents relative to the compound of formula II.

In embodiments in which two or more sulfonic acids are present, it is preferred that the total amount of all sulfonic acids present in the reaction is from about 1 to about 10 equivalents of sulfonic acids relative to the compound of formula II. For example, in embodiments in which the two sulfonic acids are present, the total amount of sulfonic acids that may be present in the reaction is preferably from 5 to 7 equivalents relative to the compound of formula II.

The sulfonic acid may be added to the reaction at any time. In particular embodiments, the compound of formula II is brought into contact with the sulfonic acid after the compound of formula II is brought into contact with the carboxylic acid.

It is stated herein that the process of the invention is performed in the presence of a carboxylic acid. The carboxylic acid may be any organic compound that contains a —C(O)OH functional group and which has a pKa of 5 or below. In particular embodiments, the carboxylic acid is a compound of formula VI,

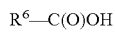   VI wherein R⁶ represents hydrogen, a $C_{1-6}$ alkyl group (optionally substituted by one or more halo atoms, hydroxyl groups or carboxylic acid groups) or an aryl group (optionally substituted by one or more halo atoms). In more particular embodiments, R⁶ represents a $C_{1-4}$ alkyl group (e.g. a $C_1$ group) optionally substituted by one or more halo atoms (for example, the carboxylic acid may be acetic acid or a halogenated derivative thereof).

In a preferred embodiment, the carboxylic acid is a mono-, di- or tri-halogenated acetic acid. The halogen is preferably selected from fluorine and chlorine, and in the case of di- and tri-halogenated acetic acids the halogen may be the same or different. Particular carboxylic acids that may be mentioned include fluoroacetic acid, chloroacetic acid, difluoroacetic acid, and, most particularly, trifluoroacetic acid, trichloroacetic acid and dichloroacetic acid. For the avoidance of doubt, mixtures of two or more of said carboxylic acids may be used in the processes described herein.

The amount of the carboxylic acid should be sufficient to enable the reaction to proceed. In particular embodiments, the amount of carboxylic acid that is present in the reaction is at least 0.1 volumes, such as from 1 to 20 volumes (e.g. from 2 to 10 volumes), relative to the compound of formula II. By the use of the term "0.1 volumes relative to the compound of formula II", etc., it is meant that the amount present is 0.1 mL per gram of the compound of formula II. In the most particular embodiments (for example, embodiments in which the carboxylic acid is trichloroacetic acid), the amount of carboxylic acid that is present in the reaction is from 2 to 9 volumes relative to the compound of formula II. In other particular embodiments (for example, embodiments in which the carboxylic acid is trifluoroacetic acid), the amount of carboxylic acid that is present in the reaction is from 3 to 6 (e.g. from 4 to 5) volumes relative to the compound of formula II.

The carboxylic acid may be added to the reaction at any time. In particular embodiments, the compound of formula II is brought into contact with the carboxylic acid before the compound of formula II is brought into contact with the sulfonic acid or the sulfide compound.

The process of the invention may be performed at room temperature or at elevated temperature. In particular embodiments of the invention, the process of the invention is performed at elevated temperature. For example, the process of the invention may be performed at temperatures greater than about 30° C., for instance greater than about 40° C. or greater than about 50° C. The upper temperature limit for the process of the invention is generally dependent upon the temperature at which decomposition of the compound of formula I becomes significant. Therefore, in particular embodiments, the process of the invention may be performed at temperatures of from about 30° C. to about 70° C. (e.g. from about 40° C. to about 60° C., such as about 50° C.).

In a further embodiment of the invention, the compound of formula I that may be separated from the solvent may be further purified by crystallisation from a suitable solvent. For instance, the compound of formula I may be dissolved to obtain a solution of that compound in a solvent (in particular, an organic solvent, e.g. an alcohol). The compound of formula I (in solvent) may be diluted with a different solvent in order to promote the crystallisation (in particular embodiments, that different solvent is an ether, such as methyl tert-butyl ether).

Preferences and options for a given aspect, feature or parameter of the invention should, unless the context indicates otherwise, be regarded as having been disclosed in combination with any and all preferences and options for all other aspects, features and parameters of the invention. For example, any preferred definitions and/or quantities for the carboxylic acid may be combined with any preferred definitions and/or quantities for the sulfonic acid.

Therefore, in a further embodiment of the invention, the process is one which comprises contacting a compound of formula II, as defined herein, or a salt thereof, with a mixture comprising:
(i) water, in an amount ranging from 0.1 to 70% by weight relative to the combined weight of the water and the compound of formula II;
(ii) a sulfonic acid of formula V,

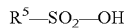    V wherein $R^5$ represents a $C_{1-6}$ alkyl group (optionally substituted by one or more halogen atoms) or an aryl group (optionally substituted by one or more substituents selected from a $C_{1-4}$ alkyl group and a halogen atom);
(iii) acetic acid, or a halogenated derivative thereof; and
(iv) a sulfide compound wherein the sulfide compound is:
  (a) a monocyclic aromatic compound containing one or more sulfur atoms within the aromatic ring;
  (b) a compound of formula IV

    IV wherein n represents from 0 to 3; or
  (c) a sulfide of formula III,

    III wherein $X^1$ and $X^2$ each independently represents hydrogen, phenyl, —C(O)$R^3$ or a $C_{1-12}$ alkyl group (optionally substituted by one or more groups selected from halogen, —NH$_2$, phenyl, —C(O)$R^4$ and —S(O)$_m$—$C_{1-4}$ alkyl);
  $R^3$ and $R^4$ independently represent —OH, —$C_{1-4}$ alkyl or —O—$C_{1-4}$ alkyl; and
  m represents from 0 to 2.

In a yet further embodiment of the invention, the process is one in which the compound of formula I is hydromorphone, and the process comprises contacting hydrocodone or a salt thereof, with a mixture comprising water and:
(i) a carboxylic acid selected from the group consisting of trifluoroacetic acid, trichloroacetic acid, difluoroacetic acid, dichloroacetic acid, fluoroacetic acid, chloroacetic acid, and mixtures thereof;
(ii) a sulfonic acid selected from the group consisting of methane sulfonic acid, trifluoromethane sulfonic acid, toluenesulfonic acid, and mixtures thereof; and
(ii) a sulfide compound selected from the group consisting of dioctyl dulfide, dibutyl sulfide, dipropyl sulfide, diethyl sulfide, dimethyl sulfide, dodecyl methyl sulfide and mixtures thereof.

In a yet further embodiment of the invention, the process is one in which the compound of formula I is hydromorphone, and the process comprises contacting hydrocodone or a salt thereof, with a mixture comprising water and:
(i) a carboxylic acid selected from the group consisting of trifluoroacetic acid, trichloroacetic acid, difluoroacetic acid, dichloroacetic acid, fluoroacetic acid, chloroacetic acid, and mixtures thereof;
(ii) a sulfonic acid selected from the group consisting of methane sulfonic acid, trifluoromethane sulfonic acid, toluenesulfonic acid, and mixtures thereof; and
(ii) a sulfide compound selected from the group consisting of dioctyl sulfide, dibutyl sulfide, dipropyl sulfide, diethyl sulfide, dimethyl sulfide, dodecyl methyl sulfide and mixtures thereof;
and further wherein:
  (a) the sulfonic acid is present at from about 1 to about 10 equivalents relative to the compound of formula II;
  (b) the sulfide compound is present in an amount of at least 1 equivalent relative to the compound of formula II;
  (c) the carboxylic acid is present in an amount of from 1 to 20 volumes relative to the compound of formula II; and/or
  (d) the water is present in an amount ranging from 0.1 to 70% by weight relative to the combined weight of the water and the compound of formula II.

In an embodiment of the invention in which the compound of formula II is hydrocodone, the process further comprises the preceding step of converting codeine to hydrocodone. This conversion may be achieved, for example, by any of the methods described hereinafter.

In an embodiment of the invention, the compound of formula II may be first formed by a process comprising reacting a compound of formula VII,

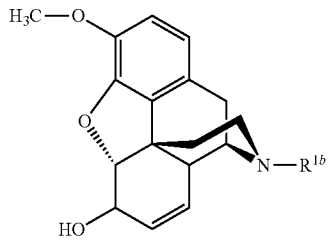    VII wherein $R^{1b}$ is defined according to $R^{1a}$
with a rhodium complex in an aqueous solvent system;
optionally wherein the compound of formula VII and the rhodium complex are mixed together with an organic additive selected from acetone, isopropanol, tert-butanol and mixtures thereof.

In particular embodiments, the rhodium complex is a rhodium (III) complex or, preferably, a rhodium (I) complex.

In the context of these processes, the term "aqueous solvent system" is intended to include solvent systems that comprise water (e.g. comprising at least 20% water) and optional additional non-aqueous solvents. Solvent systems that may be mentioned in this respect include water and mixtures of water with one or more alcohols (e.g. methanol, ethanol, isopropanol, tert-butanol or ethylene glycol).

In embodiments of the invention which involve reacting a compound of formula VII with a rhodium complex in an aqueous solvent system to form a compound of formula II, that process may comprise an initial step of reacting a compound of either formula VIII or IX, as defined below, with a compound of formula X, as defined below. This initial step may be performed in the presence of the compound of formula VII.

In embodiments of the invention which involve reacting a compound of formula VII with a rhodium complex in an aqueous solvent system to form a compound of formula II, the rhodium complex is a water-soluble rhodium complex. The term "water-soluble rhodium complex" when used herein refers to a rhodium-containing complex which has a solubility in water of at least 0.01 g per 100 g (i.e. at least 0.1 g/L) water at 20° C.

When the phosphine contains two, or particularly, one phosphorus atom capable of coordinating to rhodium, formation of the rhodium complex may be achieved by mixing the water-soluble phosphine and the precursor rhodium complex in a molar ratio (of phospine:rhodium precursor) of at least 1:1 (e.g. at least 1.5:1), in particular from 1:1 to 3:1 (such as about 2:1). The formation of the rhodium complex may be conducted in a suitable solvent, for instance any solvent that allows the dissolution of the rhodium complex. Solvents that may be mentioned in this respect include water, and mixtures of water with one or more polar organic solvents such as alcohols (e.g. methanol, ethanol, isopropanol or tert-butanol), dimethyl formamide (DMF), dimethyl sulfoxide (DMSO), or ketone-based solvents (e.g. acetone, butanone or methyl isobutyl ketone).

In embodiments of the invention which involve reacting a compound of formula VII with a rhodium complex in an aqueous solvent system to form a compound of formula II, the rhodium complex is a rhodium complex that is prepared from a water-soluble phosphine and either a precursor rhodium complex of formula VIII, $$[Rh(diene)L_{n'}]^{+}X^{-} \qquad \text{VIII}$$

or a dimeric precursor rhodium complex of formula IX, $$[Rh(diene)(Hal)]_2 \qquad \text{IX}$$

wherein diene represents a diene ligand such as COD (1,5-cyclooctadiene), bicyclo[2,2,1]heptadiene or norbornadiene, $X^-$ represents a suitable anion (such as a halide or, particularly, a non-coordinating anion, such as BARF (i.e. a tetrakis(polyfluoroaryl)borate), $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ or $PhCO_2^-$), L represents a neutral ligand (for example a weakly coordinating ligand such as acetonitrile, acetone, DMF, THF, DMSO or benzonitrile), n' represents from 1 to 3 (e.g. 2), and Hal represents a halide (such as chloride) or a hydroxide.

In particular embodiments of such processes, the rhodium complex is prepared from $[Rh(COD)(CH_3CN)_2](BF_4)$ and a phosphine derivative (e.g. a water-soluble phosphine derivative).

Water-soluble phosphines which may be used in such processes include phosphines having a water-solubility of at least 0.1 g per 100 g water at 20° C. (i.e. 1 g/L). In particular embodiments, the water-soluble phosphine has a solubility in water of at least 0.5 g (e.g. at least 5 g) per 100 g (i.e. at least 5 g/L (e.g. at least 50 g/L)) water at 20° C.

Particular phosphines that may be mentioned include:

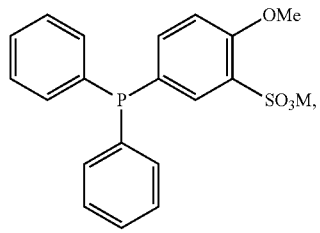

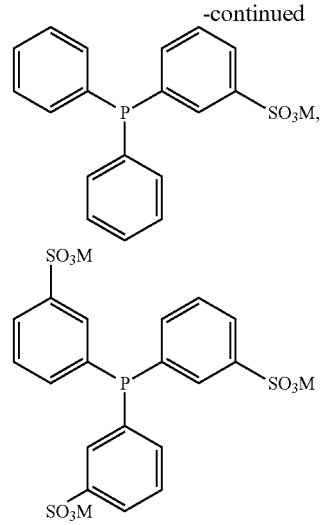

and 1,3,5-triaza-7-phosphaadamantane (PTA), which latter phosphine is optionally alkylated with one or more (e.g. one) methyl groups (thus including 1-methyl-1,3,5-triaza-7-phosphaadamantane); wherein M represents an alkali metal selected from lithium, cesium and, particularly, potassium and sodium.

A particular rhodium complex that may be mentioned in this respect is that formed by reacting [Rh(COD)(CH$_3$CN)$_2$](BF$_4$) with 1,3,5-triaza-7-phosphaadamantane or a derivative thereof.

The amount of the organic additive should be sufficient to reduce the amount of enone by-product in the product of the reaction compared to the product produced in the absence of an organic additive. In particular embodiments, the amount of organic additive that is present in the reaction is at least 0.5 equivalents, such as from 1 to 20 equivalents (e.g. from 7 to 9 equivalents), relative to the compound of formula II.

In one embodiment:
(i) the compound of formula II is provided in a suitable solvent system, as defined above;
(ii) the rhodium complex is provided in an aqueous solvent system (e.g. a solvent system that consists predominantly of water);
(iii) the organic additive is added to the compound of formula II; and then
(iv) the solution comprising the rhodium complex is added to the mixture comprising the compound of formula II and the organic additive.

In another embodiment of the present invention, particularly one in which the compound of formula II is hydrocodone, the compound of formula II may be formed from thebaine. Thus, there is provided a process for forming hydromorphone, wherein the process comprises:
(i) converting thebaine to hydrocodone; and
(ii) converting said hydrocodone to hydromorphone according to a process as described herein.

The conversion of thebaine to hydrocodone may be achieved by any method known to the skilled person. For example, U.S. Pat. No. 8,399,671 discloses a process for reducing thebaine using hydrazine to form 8,14-dihydrothebaine. 8,14-Dihydro-thebaine is then hydrolysed to form hydrocodone. Any suitable source of hydrazine, such as p-toluene sulfonyl hydrazide, may be used for the reduction step. Similarly the hydrolysis may be achieved by bringing the thebaine derivative into contact with a strong acid, such as conc. HCl, in the presence of water.

In a further embodiment of the invention there is provided a process for preparing a pharmaceutical formulation comprising a compound of formula I, or a salt thereof, as defined above, which process comprises the steps of:
(i) preparing a compound of formula I by demethylating a compound of formula II, as defined above, according to any one of the processes disclosed herein;
(ii) optionally isolating and/or purifying the compound of formula I (or a salt thereof) obtained from step (i); and
(iii) bringing into association the compound of formula I so formed (or a salt thereof) with one or more pharmaceutically-acceptable excipients, adjuvants, diluents or carriers.

Thus, in a further embodiment there is provided a pharmaceutical composition comprising hydromorphone, or a salt thereof, obtained by any one of the processes disclosed herein, and one or more pharmaceutically acceptable excipients, diluents or carriers.

In a yet further embodiment of the invention there is provided a process for preparing a salt of a compound of formula I, as defined above, which process comprises the steps of:
(i) preparing a compound of formula I by demethylating a compound of formula II, as defined above, according to any one of the processes disclosed herein;
(ii) optionally isolating and/or purifying the compound of formula I obtained from that process; and
(iii) bringing into association the compound of formula I so formed with an acid (e.g. an organic acid) under reaction conditions known to those skilled in the art, for example in the presence of a solvent (e.g. water, an alcohol (such as methanol or ethanol), acetonitrile, DMF, DMSO, or a mixture thereof) for example at or above room temperature (e.g. from room temperature to 105° C.), followed by removal of any solvent to afford the isolated salt. The salt obtained in this method, or any other, may also be converted into a different salt by any process known to a person skilled in the art.

In a yet further embodiment of the invention there is provided a process for preparing a prodrug of a compound of formula I, as defined herein, which process comprises the steps of:
(i) preparing a compound of formula I in accordance with any of the processes defined hereinabove;
(ii) optionally isolating and/or purifying the compound of formula I obtained from that process; and
(iii) converting the compound of formula I into a prodrug of the compound of formula I.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved in vivo when such prodrug is administered to a mammalian subject. The modifications typically are achieved by synthesising the parent compound (i.e. the compound of formula I) with a prodrug substituent. Prodrugs include compounds of the invention wherein a hydroxyl, amino, sulfhydryl, carboxy or carbonyl group in a compound of formula I is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Particular examples of prodrugs of compounds of formula I include those in which an enol tautomer (of the ketone groups) is derivatised with an aryl carboxylic acid (such as benzoic acid) to form an ester. The chemical conjugation of aryl carboxylic acids (such as benzoic acid) to hydrocodone is disclosed in U.S. Pat. No. 8,461,137. In such processes, the chemical bond between the two moieties can be established by reacting the enol tautomer of a compound of formula I with an activated carboxylic acid function of an aryl carboxylic acid to create an enol-ester conjugate.

The products of the process described herein may be purified via a purification step following the conversion of the compound of formula II to the compound of formula I.

The purification step may be performed in order to reduce the levels of certain impurities present in the product of the conversion step. Such impurities include derivatives of compounds of formula I which derivatives contain one or more additional unsaturations, for example compounds in which the cyclohexanone ring portion contains an $\alpha,\beta$-unsaturated ketone.

The amount of $\alpha,\beta$-unsaturated ketone derivative (e.g. codeinone) present in a given sample may be determined by any conventional method known to the person skilled in the art, such as LC-MS with SIR, or any method disclosed herein.

In a second aspect of the present invention, there is provided a process for forming a hydrochloride salt of a compound of formula I, wherein the compound of formula I is made by a process described herein in respect of the first aspect of the invention.

The processes described herein may be operated as a batch process or operated as a continuous process and may be conducted on any scale.

In general, the processes described herein may have the advantage that the compounds of formula I may be produced in a manner that utilises fewer reagents and/or solvents, and/or requires fewer reaction steps (e.g. distinct/separate reaction steps) compared to processes disclosed in the prior art. Processes described herein may also have the advantage that fewer undesired by-products (resultant of undesired side reactions) may be produced, for example, by-products that may be toxic or otherwise dangerous to work with, e.g. corrosive, and achieves high levels of conversion whilst avoiding the need to include difficult and/or expensive purification steps. The processes may also be more economical or efficient than those described in the prior art.

The processes of the invention may also have the advantage that the compound of formula I is produced in higher yield, in higher purity, in higher selectivity, in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention.

The processes may have the advantage that the compounds of formula I that are produced contain low levels of potentially genotoxic impurities (PGIs). The use of water in the process of the invention provides an economically beneficial process in which fewer impurities are formed thus potentially reducing the level of purification that may be required. In particular, it is desirable to reduce the amount of certain impurities that may be formed, particularly α,β-unsaturated ketones, as these impurities may be toxic and/or harmful to the environment.

The following examples are merely illustrative examples of the processes of the invention described herein.

All equipment, reagents and solvents used were standard laboratory equipment, e.g. glassware, heating apparatus and HPLC apparatus.

EXAMPLES

Example 1—Demethylation of Hydrocodone Using TCA

To a 5 L jacketed reactor with reflux condenser and vacuum line was added hydrocodone base (651.2 g; equivalent to 323.00 g (18.21 mol) hydrocodone dry base and 328.21 g water), TCA (2632.5 g; 1615.0 mL), dibutylsulfide (315.7 g; 376.7 mL), and MSA (311.1 g, 210.2 mL). The mixture was heated to 40° C. TfOH (404.8 g, 238.7 mL) was added. The mixture was stirred at 48±5° C. for at least 12 hr. The reaction was considered complete when the hydrocodone level was found to be not more than 4% using UPLC MD-40-14.

The batch was then cooled to 20° C. MEK (780.0 g, 969.0 mL) was then charged slowly to the mixture. The batch was cooled to ca. 20° C. and transferred to a 10 L reactor with bath set to 20° C. iPrOAc (1475.3 g, 1695.8 mL) was added to the 5 L reactor, stirred for 5 min, and then transferred to the 10 L reactor. iPrOAc (4425.9 g, 5087.3 mL) was added and the mixture was stirred at room temperature for at least 48 hr. The batch was filtered, and the cake was washed with IPAc (562.0 g, 646.0 mL). The cake was dried in vacuum at room temperature to give the crude hydromorphone triflate (281.81 g as a white solid).

Example 2—Demethylation of Hydrocodone Using TFA

To a 1 L jacketed reactor, was added hydrocodone (22.22 g), TFA (163.8 g, 110.0 mL), dibutylsulfide (21.5 g, 25.7 mL) and MSA (42.4 g, 28.6 mL). Water was added (3.1 g, 3.1 mL), and the mixture was stirred for at least 16 hr at 50±5° C. The reaction was monitored using UPLC MD-40-14, and was considered completed when the hydrocodone level was found to be less than 2.0% with only hydrocodone and hydromorphone being integrated. After completion, the batch was cooled to 20±5° C.

The product of the preceding reaction step was added to a source of chloride ions and an anti-solvent, and the resulting mixture furnished a slurry. The solid product was obtained by filtration, washed, and dried in vacuum at 20±5° C. to give 17.74 g of crude hydromorphone hydrochloride as a white to off-white solid.

Example 3—Sulfides

Demethylation reactions using hydrocodone were studied using a range of sulfides.

| Sulfide | Details | HM Area % | HC Area % | Tot Imp Area % |
|---|---|---|---|---|
| None | MSA (22.6 eq), 30° C. 16 hr | 0.0 | 86.8 | 13.2 |
| Methionine (3.0 eq) | MSA (22.6 eq), , 30° C. 16 hr | 38.6 | 47.8 | 13.5 |
| Dipropylsulfide(3.0 eq) | MSA (22.6 eq), 30° C. 16 hr | 61.1 | 10.8 | 28.1 |
| Dibutylsulfide (3.0 eq) | MSA (22.6 eq), 30° C. 16 hr | 50.1 | 24.0 | 25.9 |
| Benzylsulfide (3.0 eq) | MSA (22.6 eq), 30° C. 16 hr | 0.3 | 0.7 | 99.0 |
| Thiophene (3.0 e) | MSA (22.6 eq), 30° C. 16 hr | 0.0 | 0.0 | 100.0 |
| Tetrahydrothiophene (3.0 eq) | MSA (22.6 eq), 30° C. 16 hr | 43.6 | 6.5 | 49.9 |
| Diethylsulfide (4 eq) | TCA (5 vol), MSA (4.0 equiv), 30° C., 16 hr | 68.6 | 21.7 | 9.7 |
| Ethylpropylsulfide (4 eq) | TCA (5 vol), MSA (4.0 equiv), 30° C., 16 hr | 79.1 | 19.4 | 1.5 |
| Dipropylsulfide (4 eq) | TCA (5 vol), MSA (4.0 equiv), 30° C., 16 hr | 69.5 | 26.0 | 3.5 |
| Dibutylsulfide (4 eq) | TCA (5 vol), MSA (4.0 equiv), 30° C., 16 hr | 65.4 | 24.8 | 9.8 |
| Diisopropylsulfide (4 eq) | TCA (5 vol), MSA (4.0 equiv), 30° C., 16 hr | 37.9 | 60.2 | 1.9 |
| Thioanisole (4 eq) | TCA (5 vol), MSA (4.0 equiv), 30° C., 16 hr | 26.6 | 47.1 | 26.3 |

The following additional sulfides were also screened (conditions: TCA 5 vol, TfOH 2.5 eq, MSA 4.0 eq, 35° C.).

| Experiment | Sulfide | HM area % | HC area % | Impurity Area % |
|---|---|---|---|---|
| 1 | Trimethylene sulfide | 9.4 | 89.1 | 1.5 |
| 2 | Thioacetic acid | 8.6 | 5.4 | 86.0 |
| 3 | Dimethyl sulfide | 74.2 | 10.2 | 15.6 |
| | | 81.0 | 3.3 | 15.7 |
| 4 | Tetrahydrothiophene | 70.0 | 15.0 | 15.0 |
| | | 75.1 | 7.9 | 17.0 |
| 5 | Diethyl sulfide | 75.1 | 16.2 | 8.7 |
| | | 88.2 | 9.1 | 2.7 |
| | | 83.1 | 0.0 | 16.9 |
| 6 | Ethyl propyl sulfide | 71.7 | 12.2 | 16.1 |
| | | 75.9 | 5.6 | 18.5 |
| | | 77.7 | 0.0 | 22.3 |
| 7 | tert-Butyl methyl sulfide | Decomposition | | |
| 8 | Cyclohexene sulfide | Decomposition | | |
| 9 | Dipropyl sulfide | 81.3 | 9.3 | 9.4 |
| | | 84.8 | 3.9 | 11.3 |
| 10 | Diisopropyl sulfide | 45.0 | 48.7 | 6.3 |
| | | 54.4 | 39.3 | 6.3 |
| | | 74.0 | 5.4 | 20.6 |

-continued

| Experiment | Sulfide | HM area % | HC area % | Impurity Area % |
|---|---|---|---|---|
| 11 | Thioanisole | 6.8 | 0.8 | 92.4 |
| 12 | Methyl (methylthio)acetate | 54.1 | 40.6 | 5.3 |
|  |  | 54.5 | 38.1 | 7.4 |
| 13 | Dibutyl sulfide | 80.2 | 13.4 | 6.4 |
|  |  | 86.3 | 6.7 | 7.0 |
|  |  | 82.9 | 0.0 | 17.1 |

-continued

| Experiment | Sulfide | HM area % | HC area % | Impurity Area % |
|---|---|---|---|---|
| 14 | sec-Dibutyl sulfide | 34.5 | 62.6 | 2.9 |
|  |  | 43.7 | 53.3 | 3.0 |
|  |  | 80.5 | 14.0 | 5.5 |
| 15 | 2,2'-Thiodiacetic acid | 11.0 | 80.3 | 8.7 |
| 16 | S-Phenyl thioacetate | Decomposition | | |
| 17 | Phenyl trifluoromethyl sulfide | 0.8 | 89.6 | 9.6 |
| 18 | 3,3'-Thiodipropionic acid | 51.0 | 23.8 | 25.2 |
|  |  | 54.4 | 13.2 | 32.4 |
| 19 | Diphenyl sulfide | 5.7 | 2.5 | 91.8 |
| 20 | Dodecyl methyl sulfide | 89.1 | 7.8 | 3.1 |
|  |  | 91.5 | 3.1 | 5.4 |
|  |  | 79.1 | 0.0 | 20.9 |
| 21 | Dioctyl sulfide | 81.4 | 14.3 | 4.3 |
|  |  | 87.0 | 7.5 | 5.5 |
|  |  | 84.9 | 0.0 | 15.1 |
| 22 | Isopropyl methyl sulfide | 71.2 | 11.0 | 17.8 |
| 23 | Pentamethylene sulfide | 66.1 | 17.9 | 16.0 |
| 24 | Butyl methyl sulfide | 66.5 | 6.0 | 27.5 |
| 25 | Ethyl isopropyl sulfide | 57.8 | 26.7 | 15.5 |
| 26 | Bis(methylthio)methane | Decomposition | | |
| 27 | Isopropyl propyl sulfide | 55.6 | 24.6 | 19.8 |
| 28 | Butyl ethyl sulfide | 63.2 | 11.1 | 25.7 |
| 29 | Methyl (methylsulfinyl)methyl sulfide | Decomposition | | |
| 30 | tert-Butyl sulfide | Decomposition | | |
| 31 | Isobutyl sulfide | 76.6 | 10.9 | 12.5 |

Example 4—Analysis of Critical Parameters for the Demethylation Reaction Using TfOH The demethylation of hydrocodone was assessed using a mixture containing hydrocodone, water, TfOH, MSA, dibutylsulfide and TCA.

Method

A scintillation vial was equipped with a magnetic stir bar and hydrocodone (1.00 g), TCA (8.15 g, 5.00 mL), MSA (0.96 g, 0.65 mL) and dibutylsulfide (0.98 g, 1.17 mL) were added.

Water and TfOH were also added in the amounts shown in the table below, and the reaction mixture was heated to 42, 48 or 54° C. (as specified in the results section) overnight.

| Reagent | MW | Density (g/mL) | Assay | Amt (g) | Amt (mL) | moles | Mole Equiv | g/g HC | mL/g HC |
|---|---|---|---|---|---|---|---|---|---|
| Hydrocodone Content |  |  |  | 1.00 |  |  |  |  |  |
| Water Content | 18.02 | 1 | 0.00% | 0.00 | 0.00 | 0.000 | 0.00 | 0.00 | 0.00 |
| Hydrocodone Base | 299.36 | 1 | 100.00% | 1.00 | 1.00 | 0.003 | 1.00 | 1.00 | 1.00 |
| Water 5% | 18.02 | 1.000 | 100% | 0.05 | 0.05 | 0.003 | 0.83 | 0.05 | 0.05 |
| Water 10% | 18.02 | 1.000 | 100% | 0.10 | 0.10 | 0.006 | 1.66 | 0.10 | 0.10 |
| Water 15% | 18.02 | 1.000 | 100% | 0.15 | 0.15 | 0.008 | 2.49 | 0.15 | 0.15 |
| TfOH 2.0 | 150.08 | 1.700 | 100% | 1.00 | 0.59 | 0.007 | 2.00 | 1.00 | 11.80 |
| TfOH 2.5 | 150.08 | 1.700 | 100% | 1.25 | 0.74 | 0.008 | 2.50 | 1.25 | 7.37 |
| TfOH 3.0 | 150.08 | 1.700 | 100% | 1.50 | 0.88 | 0.010 | 3.00 | 1.50 | 5.90 |
| MSA 3.0 | 96.11 | 1.480 | 100% | 0.96 | 0.65 | 0.010 | 3.00 | 0.96 | 0.65 |
| Dibutylsulfide 2.0 | 146.29 | 0.838 | 100% | 0.98 | 1.17 | 0.007 | 2.00 | 0.98 | 1.17 |
| TCA 5.0 | 163.39 | 1.630 | 100% | 8.15 | 5.00 | 0.050 | 14.93 | 8.15 | 5.00 |
| Hydromorphone Base | 285.34 | 1 | 100% | 0.95 | 0.95 | 0.003 | 1.00 | 0.95 | 0.95 |

Results

The table below shows the results obtained after a reaction time of 24 hrs using different amounts of water and TfOH, and different reaction temperatures. The water quantity is expressed as % by weight relative to the hydrocodone. The TfOH quantity is expressed as molar equivalents relative to the hydrocodone.

| Exp | Temp (° C.) | Water (%) | TfOH (eq) | HM area % | HC area % | Impurity Area % |
|---|---|---|---|---|---|---|
| 1 | 42 | 5 | 2 | 88.6 | 1.2 | 10.2 |
| 5 | 42 | 5 | 3 | 86.2 | 0.1 | 13.7 |
| 9 | 42 | 10 | 2.5 | 87.6 | 1.4 | 11.0 |
| 3 | 42 | 15 | 2 | 85.3 | 7.8 | 6.9 |
| 7 | 42 | 15 | 3 | 88.4 | 0.9 | 10.7 |
| 11 | 48 | 5 | 2.5 | 82.9 | 0.1 | 17.0 |
| 13 | 48 | 10 | 2 | 86.7 | 1.1 | 12.2 |
| 17 | 48 | 10 | 2.5 | 84.8 | 0.1 | 15.1 |
| 15 | 48 | 10 | 2.5 | 84.1 | 0.1 | 15.8 |
| 16 | 48 | 10 | 2.5 | 84.4 | 0.1 | 15.5 |
| 14 | 48 | 10 | 3 | 83.4 | 0.1 | 16.5 |
| 12 | 48 | 15 | 2.5 | 86.6 | 0.8 | 12.6 |
| 2 | 54 | 5 | 2 | 77.0 | 0.1 | 22.9 |
| 6 | 54 | 5 | 3 | 71.8 | 0.1 | 28.1 |
| 10 | 54 | 10 | 2.5 | 78.8 | 0.1 | 21.2 |
| 4 | 54 | 15 | 2 | 83.0 | 0.1 | 16.9 |
| 8 | 54 | 15 | 3 | 79.0 | 0.1 | 20.9 |

It was found that increased levels of water led to an increase in the amount of hydromorphone produced, a decrease in the level of impurities, and a slowing of the conversion of hydrocodone.

Example 5—Analysis of Critical Parameters for the Demethylation Reaction Using TfOH The demethylation of hydrocodone was assessed using a mixture containing hydrocodone, water, TfOH, MSA, dibutylsulfide and TCA.

Method

A scintillation vial was equipped with a magnetic stir bar and hydrocodone (1.00 g), TCA (8.15 g, 5.00 mL), TfOH (1.25 g, 0.74 mL), MSA (0.96 g, 0.65 mL) and dibutylsulfide (0.98 g, 1.17 mL) were added. Water was also added in the amount shown in the table below, and the reaction mixture was heated to 44, 48 or 52° C. (as specified in the results section) overnight

| Reagent | MW | Density (g/mL) | Assay | Amt (g) | Amt (mL) | moles | Mole Equiv | g/g HC | mL/g HC |
|---|---|---|---|---|---|---|---|---|---|
| Hydrocodone Content | | | | 1.00 | | | | | |
| Water Content | 18.02 | 1 | 0.00% | 0.00 | 0.00 | 0.000 | 0.00 | 0.00 | 0.00 |
| Hydrocodone Base | 299.36 | 1 | 100.00% | 1.00 | 1.00 | 0.003 | 1.00 | 1.00 | 1.00 |
| Water 5% | 18.02 | 1.000 | 100% | 0.05 | 0.05 | 0.003 | 0.83 | 0.05 | 0.05 |
| Water 10% | 18.02 | 1.000 | 100% | 0.10 | 0.10 | 0.006 | 1.66 | 0.10 | 0.10 |
| Water 15% | 18.02 | 1.000 | 100% | 0.15 | 0.15 | 0.008 | 2.49 | 0.15 | 0.15 |
| TfOH 2.5 | 150.08 | 1.700 | 100% | 1.25 | 0.74 | 0.008 | 2.50 | 1.25 | 7.37 |
| MSA 3.0 | 96.11 | 1.480 | 100% | 0.96 | 0.65 | 0.010 | 3.00 | 0.96 | 0.65 |
| Dibutylsulfide 2.0 | 146.29 | 0.838 | 100% | 0.98 | 1.17 | 0.007 | 2.00 | 0.98 | 1.17 |
| TCA 5.0 | 163.39 | 1.630 | 100% | 8.15 | 5.00 | 0.050 | 14.93 | 8.15 | 5.00 |
| Hydromorphone Base | 285.34 | 1 | 100% | 0.95 | 0.95 | 0.003 | 1.00 | 0.95 | 0.95 |

Results

The table below shows the results obtained after the specified reaction time (20.5 or 44 hrs) using different amounts of water, and different reaction temperatures. The water quantity is expressed as % by weight relative to the hydrocodone.

| | | | | 20.5 hr | | | 44 hr | | |
|---|---|---|---|---|---|---|---|---|---|
| Exp | Added Water | Calculated Water | Temp (° C.) | HM area % | HC area % | Impurity Area % | HM area % | HC area % | Impurity Area % |
| 1 | 5% | 14.4% | 44 | 88.8 | 5.9 | 5.3 | 87.6 | 0.4 | 12.0 |
| 7 | 10% | 20.0% | 44 | 86.6 | 8.8 | 4.6 | 91.0 | 0.8 | 8.1 |
| 2 | 15% | 23.4% | 44 | 82.8 | 13.4 | 3.8 | 90.9 | 2.9 | 6.2 |
| 5 | 5% | 13.3% | 48 | 91.5 | 1.4 | 7.1 | 87.6 | 0.1 | 12.3 |
| 9 | 10% | 18.4% | 48 | 89.4 | 5.8 | 4.8 | 90.4 | 0.5 | 9.1 |
| 10 | 10% | 18.7% | 48 | 89.7 | 3.9 | 6.4 | 89.8 | 0.3 | 9.9 |
| 11 | 10% | 19.1% | 48 | 90.1 | 4.0 | 5.9 | 90.2 | 0.2 | 9.6 |
| 6 | 15% | 24.5% | 48 | 88.3 | 7.0 | 4.7 | 91.3 | 0.6 | 8.1 |
| 3 | 5% | 15.9% | 52 | 90.3 | 0.7 | 9.0 | 85.4 | 0.0 | 14.6 |
| 8 | 10% | 20.0% | 52 | 89.3 | 0.8 | 9.9 | 86.3 | 0.1 | 13.6 |
| 4 | 15% | 25.4% | 52 | 88.3 | 6.3 | 5.4 | 90.1 | 0.6 | 9.3 |

It was found that the effect of water on the hydromorphone response changes over time from slowing the reaction down (less area % hydromorphone) to having a preservative effect on hydromorphone. Increasing the levels of water inhibited the formation of by products and inhibited the conversion of hydrocodone.

Example 6—Analysis of Critical Parameters for the Demethylation Reaction Using MSA The demethylation of hydrocodone was assessed using a mixture containing hydrocodone, water, MSA, dibutylsulfide and TFA.

Method

A scintillation vial was equipped with a magnetic stir bar and hydrocodone (1.00 g), TFA (8.94 g, 6.00 mL), and dibutylsulfide (1.222 g, 1.458 mL) were added. Water and MSA were also added in the amount shown in the table below, and the reaction mixture was heated to 45, 50 or 55° C. (as specified in the results section) overnight.

| Reagent | MW | Density (g/mL) | Assay | Amt (g) | Amt (mL) | moles | Mole Equiv | g/g HC | mL/g HC |
|---|---|---|---|---|---|---|---|---|---|
| Hydrocodone Content | | | | 1.0 | | | | | |
| Water Content | 18.02 | 1.0 | 0.00% | 0.00 | 0.00 | 0.000 | 0.00 | 0.0 | 0.0 |
| Hydrocodone Base | 299.36 | 1.0 | 100.00% | 1.00 | 1.00 | 0.0033 | 1.00 | 1.0 | 1.0 |
| Dibutylsulfide 1.5 | 146.29 | 0.838 | 100% | 0.73 | 0.875 | 0.0050 | 1.50 | 0.73 | 0.87 |
| Dibutylsulfide 2.0 | 146.29 | 0.838 | 100% | 0.98 | 1.166 | 0.0067 | 2.00 | 0.98 | 1.17 |
| Dibutylsulfide 2.5 | 146.29 | 0.838 | 100% | 1.22 | 1.458 | 0.0084 | 2.50 | 1.22 | 1.46 |
| TFA 4 | 114.02 | 1.49 | 100% | 5.96 | 4.00 | 0.052 | 15.65 | 5.960 | 4.00 |
| TFA 5 | 114.02 | 1.49 | 100% | 7.45 | 5.00 | 0.065 | 19.56 | 7.450 | 5.00 |
| TFA 6 | 114.02 | 1.49 | 100% | 8.94 | 6.00 | 0.078 | 23.47 | 8.940 | 6.00 |
| MSA 4 | 96.11 | 1.48 | 100% | 1.28 | 0.87 | 0.0134 | 4.00 | 1.28 | 0.54 |
| MSA 5 | 96.11 | 1.48 | 100% | 1.61 | 1.08 | 0.0167 | 5.00 | 1.61 | 21.69 |
| MSA 6 | 96.11 | 1.48 | 100% | 1.93 | 1.30 | 0.0200 | 6.00 | 1.93 | 13.02 |
| Water 1% | 18.01 | 1.000 | 100% | 0.010 | 0.010 | 0.001 | 0.17 | 0.01 | 0.01 |
| Water 5% | 18.01 | 1.000 | 100% | 0.050 | 0.050 | 0.003 | 0.83 | 0.05 | 0.05 |
| Water 9% | 18.01 | 1.000 | 100% | 0.100 | 0.100 | 0.006 | 1.66 | 0.10 | 0.10 |

Results

The table below shows the results obtained after 24 hrs using different amounts of water and MSA, and different reaction temperatures. The water quantity is expressed as % by weight relative to the hydrocodone. The MSA quantity is expressed as molar equivalents relative to the hydrocodone.

| Exp | MSA | Water | Temperature | TFA | Dibutylsulfide | HM | HC | Impurity |
|---|---|---|---|---|---|---|---|---|
| 1 | 4 | 1 | 45 | 5 | 2 | 87.9 | 8.7 | 3.4 |
| 2 | 6 | 1 | 45 | 5 | 2 | 90.7 | 3.3 | 6 |
| 3 | 4 | 9 | 45 | 5 | 2 | 83.8 | 13.7 | 2.5 |
| 4 | 6 | 9 | 45 | 5 | 2 | 88.6 | 7.9 | 3.5 |
| 5 | 4 | 1 | 55 | 5 | 2 | 89.3 | 1 | 9.7 |
| 6 | 6 | 1 | 55 | 5 | 2 | 86.7 | 0.1 | 13.2 |
| 7 | 4 | 9 | 55 | 5 | 2 | 90.1 | 2.2 | 7.7 |
| 8 | 6 | 9 | 55 | 5 | 2 | 89.7 | 0.5 | 9.8 |
| 9 | 5 | 5 | 50 | 5 | 2 | 90.6 | 2.9 | 6.5 |
| 10 | 5 | 5 | 50 | 5 | 2 | 90.6 | 3 | 6.4 |
| 11 | 5 | 5 | 50 | 5 | 2 | 90.4 | 3.4 | 6.2 |

It was found that the reaction rate is influenced by water, i.e higher water levels slowed the conversion to hydromorphone. Also, less hydrocodone remains when the reaction is conducted at higher temperatures or with greater quantities of MSA. Increased levels of water resulted in lower levels of impurities.

Example 7—Analysis of Critical Parameters for the Demethylation Reaction Using MSA The demethylation of hydrocodone was assessed using a mixture containing hydrocodone, water, MSA, dibutylsulfide and TFA.

Method

A scintillation vial was equipped with a magnetic stir bar and hydrocodone (1.00 g), TFA (7.450 g, 5.000 mL), and dibutylsulfide (0.977 g, 1.166 mL) were added. Water and MSA were also added in the amount shown in the table below, and the reaction mixture was heated to 47, 50 or 53° C. (as specified in the results section) overnight.

| Reagent | MW | Density (g/mL) | Assay | Amt (g) | Amt (mL) | moles | Mole Equiv | g/g HC | mL/g HC |
|---|---|---|---|---|---|---|---|---|---|
| Hydrocodone Content | | | | 1.0 | | | | | |
| Water Content | 18.02 | 1.0 | 0.00% | 0.000 | 0.000 | 0.000 | 0.00 | 0.0 | 0.0 |
| Hydrocodone Base | 299.36 | 1.0 | 100.00% | 1.000 | 1.000 | 0.0033 | 1.00 | 1.0 | 1.0 |
| Dibutylsulfide 2 | 146.29 | 0.838 | 100% | 0.977 | 1.166 | 0.0067 | 2.00 | 0.98 | 1.17 |
| TFA 5 | 114.02 | 1.49 | 100% | 7.450 | 5.000 | 0.065 | 19.56 | 7.450 | 5.00 |
| MSA 5 | 96.11 | 1.48 | 100% | 1.605 | 1.085 | 0.0167 | 5.00 | 1.61 | 0.56 |
| MSA 6 | 96.11 | 1.48 | 100% | 1.926 | 1.302 | 0.0200 | 6.00 | 1.93 | 65.08 |
| MSA 7 | 96.11 | 1.48 | 100% | 2.247 | 1.518 | 0.0234 | 7.00 | 2.25 | 37.96 |
| Water 2% | 18.01 | 1.000 | 100% | 0.020 | 0.020 | 0.001 | 0.33 | 0.02 | 0.02 |
| Water 4% | 18.01 | 1.000 | 100% | 0.040 | 0.040 | 0.002 | 0.66 | 0.04 | 0.04 |

Results

The table below shows the results obtained after 21 hrs using different amounts of water and MSA, and different reaction temperatures. The water quantity is expressed as % by weight relative to the hydrocodone. The MSA quantity is expressed as molar equivalents relative to the hydrocodone.

| Exp | Temperature (° C.) | Water | MSA | HM % | HC % | Impurity % |
|---|---|---|---|---|---|---|
| 1 | 47 | 0 | 5 | 89.5 | 5.3 | 5.2 |
| 2 | 53 | 0 | 5 | 88.5 | 1.1 | 10.4 |
| 3 | 47 | 4 | 5 | 88.3 | 7.4 | 4.3 |
| 4 | 53 | 4 | 5 | 89.4 | 1.9 | 8.7 |
| 5 | 47 | 0 | 7 | 90 | 2 | 8 |
| 6 | 53 | 0 | 7 | 85.4 | 0.5 | 14.1 |
| 7 | 47 | 4 | 7 | 90.6 | 2.1 | 7.3 |
| 8 | 53 | 4 | 7 | 88.5 | 0.8 | 10.7 |
| 9 | 47 | 2 | 6 | 90.3 | 4.8 | 4.9 |
| 10 | 53 | 2 | 6 | 88.4 | 0.8 | 10.8 |
| 11 | 50 | 0 | 6 | 90.6 | 1.8 | 7.6 |
| 12 | 50 | 4 | 6 | 90.4 | 1.9 | 7.7 |
| 13 | 50 | 2 | 5 | 90.1 | 3.3 | 6.6 |
| 14 | 50 | 2 | 7 | 89.7 | 0.4 | 9.9 |
| 15 | 50 | 2 | 6 | 90.5 | 2 | 7.5 |
| 16 | 50 | 2 | 6 | 90 | 2 | 8 |
| 17 | 50 | 2 | 6 | 90.2 | 1.8 | 8 |

It was found that increased levels of water in the reactions led to increased formation of hydromorphone, slower conversion of hydrocodone to hydromorphone and lower levels of impurities. Higher temperatures led to increased degradation of hydromorphone and conversion of hydrocodone. Also, more impurities were formed when the reaction was performed at higher temperatures.

Example 8—Analysis of Critical Parameters for the Demethylation Reaction Using MSA The demethylation of hydrocodone was assessed using a mixture containing hydrocodone, water, MSA, dibutylsulfide and either TFA or TCA.

Method

A scintillation vial was equipped with a magnetic stir bar and hydrocodone (1.00 g) and dibutylsulfide (0.977 g, 1.166 mL) were added along with either TFA (7.450 g, 5.000 mL) or TCA (8.2 g, 5.000 mL). Water and MSA were also added in the amount shown in the table below, and the reaction mixture was heated to 50° C. overnight.

| Reagent | MW | Density (g/mL) | Assay | Amt (g) | Amt (mL) | moles | Mole Equiv | g/g HC | mL/g HC |
|---|---|---|---|---|---|---|---|---|---|
| Hydrocodone Content | | | | 1.00 | | | | | |
| Water Content | 18.02 | 1 | 0.000% | 0.000 | 0.0 | 0.000 | 0.00 | 0.00 | 0.00 |
| Hydrocodone Base | 299.36 | 1 | 100.0% | 1.0 | 1.0 | 0.003 | 1.00 | 1.00 | 1.00 |
| Dibutylsulfide | 146.29 | 0.838 | 100% | 1.0 | 1.2 | 0.007 | 2.00 | 0.98 | 1.17 |
| TCA 5 | 163.39 | 1.63 | 100% | 8.2 | 5.0 | 0.050 | 14.93 | 8.15 | 5.00 |
| TFA 5 | 114.02 | 1.489 | 100% | 7.4 | 5.0 | 0.065 | 19.55 | 7.45 | 5.00 |
| MSA 5.0 | 96.11 | 1.480 | 100% | 1.6 | 1.1 | 0.017 | 5.00 | 1.61 | 0.13 |
| MSA 6.0 | 96.11 | 1.480 | 100% | 1.9 | 1.3 | 0.020 | 6.00 | 1.93 | 0.17 |
| MSA 7.0 | 96.11 | 1.480 | 100% | 2.2 | 1.5 | 0.023 | 7.00 | 2.25 | 0.95 |
| Water 5% | 18.00 | 1.000 | 100% | 0.1 | 0.05 | 0.003 | 0.83 | 0.05 | 0.05 |
| Water 15% | 18.00 | 1.000 | 100% | 0.2 | 0.15 | 0.008 | 2.49 | 0.15 | 0.15 |
| Water 25% | 18.00 | 1.000 | 100% | 0.3 | 0.25 | 0.014 | 4.16 | 0.25 | 0.25 |
| Hydromorphone HCl | 321.80 | 1.0 | 100% | 1.1 | 1.1 | 0.003 | 1.00 | 1.07 | 1.07 |

Results

The table below shows the results obtained after the times specified using different amounts of water and MSA, and either TCA or TFA. The water quantity is expressed as % by weight relative to the hydrocodone. The MSA quantity is expressed as molar equivalents relative to the hydrocodone.

| Exp | Water | MSA | Solvent | Hydromorphone 24 h | Hydromorphone 43 h | Hydrocodone 24 h | Hydrocodone 43 h | Impurities 24 h | Impurities 43 h |
|---|---|---|---|---|---|---|---|---|---|
| 1 | 5 | 5 | TFA | 88.1 | 88.2 | 7.2 | 0.2 | 4.7 | 11.6 |
| 2 | 25 | 5 | TFA | 80 | 89.6 | 16.9 | 3.5 | 3.1 | 6.9 |
| 3 | 5 | 7 | TFA | 90.3 | 84.6 | 2.1 | 0.1 | 7.6 | 15.3 |
| 4 | 25 | 7 | TFA | 85.7 | 89.7 | 10.2 | 0.9 | 4.1 | 9.4 |
| 5 | 5 | 5 | TCA | 88.6 | 91.2 | 8.5 | 0.8 | 2.9 | 8 |
| 6 | 25 | 5 | TCA | 64.2 | 81.8 | 34.3 | 16 | 1.5 | 2.2 |
| 7 | 5 | 7 | TCA | 91 | 90 | 3.9 | 0.1 | 5.1 | 9.9 |
| 8 | 25 | 7 | TCA | 80.9 | 90.6 | 16.9 | 4.3 | 2.2 | 5.1 |
| 9 | 15 | 6 | TFA | 87.8 | 88.8 | 7.3 | 0.7 | 4.9 | 10.5 |
| 10 | 15 | 6 | TFA | 87.3 | 89.4 | 8.3 | 0.6 | 4.4 | 10 |
| 11 | 15 | 6 | TFA | 86.7 | 89.1 | 9.1 | 0.6 | 4.2 | 10.3 |
| 12 | 15 | 6 | TCA | 85.3 | 91.6 | 12.1 | 3.1 | 2.6 | 5.3 |
| 13 | 15 | 6 | TCA | 83.1 | 91.5 | 14.6 | 3.6 | 2.3 | 4.9 |
| 14 | 15 | 6 | TCA | 82.3 | 90.9 | 15.4 | 3.9 | 2.3 | 5.2 |

It was found that increased levels of water in the reactions led to a slowing of the reaction initially, but also a slowing of further degradation of hydromorphone. Water gave a slower conversion of hydrocodone throughout the time of the experiment, and increased levels of water led to lower levels of impurities.

ABBREVIATIONS

DMF Dimethylformamide
GC Gas chromatography
HC Hydrocodone
HM Hydromorphone
HPLC High performance liquid chromatography
hr Hours
iPrOAc Isopropyl acetate
iPrOH Isopropyl alcohol
KF Karl Fischer
MEK Methyl ethyl ketone
MeOH Methanol
MSA Methane sulfonic acid
MTBE Methyl-tert-butyl ether
MW Molecular weight
NMR Nuclear magnetic resonance
rt Room temperature
TCA Trichloroacetic acid
TFA Trifluoroacetic acid
TfOH Trifluoromethane sulfonic acid
UPLC Ultra performance liquid chromatography

The invention claimed is:

1. A process for the preparation of a compound of formula I,

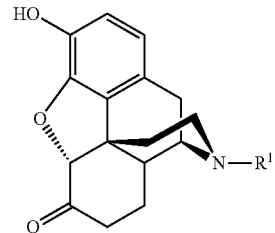

(I)

or a pharmaceutically acceptable salt thereof;
wherein:
$R^1$ represents hydrogen, $C_{1-12}$ alkyl, $C_{2-12}$ alkenyl, $C_{2-12}$ alkynyl or $C_{3-12}$ cycloalkyl, wherein the alkyl, alkenyl, alkynyl and cycloalkyl (which latter four groups are optionally substituted by one or more halogen atoms or phenyl groups;
the process comprises contacting a compound of formula II,

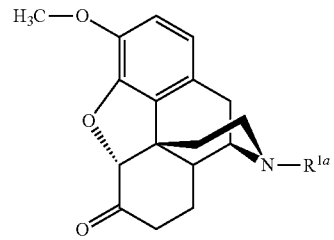

II or a salt thereof, wherein $R^{1a}$ is defined according to $R^1$, with a mixture comprising water, a carboxylic acid, a sulfonic acid, and a sulfide compound;
wherein the water is present in the mixture at from about 0.1% to about 70% by weight relative to combined weight of the water and the compound of formula II, and the sulfide compound is selected from the group consisting of cyclic sulfur-containing compounds and sulfides of formula III,

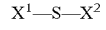

III wherein $X^1$ and $X^2$ each independently represent hydrogen, phenyl, —C(O)$R^3$ or a $C_{1-12}$ alkyl group, wherein the phenyl, $R^3$ and alkyl are each independently optionally substituted by one or more substituents selected from the group consisting of halogen, —OH, —NH$_2$, phenyl, —O—$C_{1-4}$ alkyl, —C(O)$R^4$ and —S(O)$_m$—$C_{1-4}$ alkyl;
$R^3$ and $R^4$ independently represent —OH, —$C_{1-4}$ alkyl or —O—$C_{1-4}$ alkyl; and
m represents from 0 to 2.

2. The process as claimed in claim 1, wherein $R^1$ represents methyl, ethyl, propyl, butyl, benzyl or —CH$_2$-cyclopropyl.

3. The process as claimed in claim 1, wherein $R^1$ represents methyl.

4. The process as claimed in claim 1, wherein the sulfonic acid is a sulfonic acid of formula V,

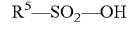

V wherein R⁵ represents a $C_{1-6}$ alkyl group that is optionally substituted by one or more halogen atoms, or an aryl group that is optionally substituted by one or more substituents selected from the group consisting of a $C_{1-4}$ alkyl group and a halogen atom.

5. The process as claimed in claim 4, wherein the sulfonic acid is selected from the group consisting of methane sulfonic acid, trifluoromethane sulfonic acid, toluenesulfonic acid, and mixtures thereof.

6. The process as claimed in claim 1, wherein the sulfonic acid is present at from about 1 to about 10 equivalents relative to the compound of formula II.

7. The process as claimed in claim 1, wherein the sulfide compound is:
   (a) a monocyclic aromatic compound containing one or more sulfur atoms within the aromatic ring;
   (b) a compound of formula IV

IV wherein n represents from 0 to 3; or
(c) a sulfide of formula III, $X^1$—S—$X^2$  III wherein $X^1$ and $X^2$ each independently represent hydrogen, phenyl, —C(O)R³ or a $C_{1-12}$ alkyl group, wherein the phenyl, R³ and alkyl are each independently optionally substituted by one or more substituents selected from the group consisting of halogen, —NH₂, phenyl, —C(O)R⁴ and —S(O)$_m$—$C_{1-4}$ alkyl);
R³ and R⁴ independently represent —OH, —$C_{1-4}$ alkyl or —O—$C_{1-4}$ alkyl; and
m represents from 0 to 2.

8. The process as claimed in claim 7, wherein the sulfide compound is selected from the group consisting of dioctyl sulfide, dibutyl sulfide, dipropyl sulfide, diethyl sulfide, dimethyl sulfide, dodecyl methyl sulfide, and mixtures thereof.

9. The process as claimed in claim 1, wherein the sulfide compound is present in an amount of at least 1 equivalent relative to the compound of formula II.

10. The process as claimed in claim 1, wherein the carboxylic acid has a pKa of 5 or below.

11. The process as claimed in claim 1, wherein the carboxylic acid is acetic acid, or a halogenated derivative thereof.

12. The process as claimed in claim 11, wherein the carboxylic acid is selected from the group consisting of trifluoroacetic acid, trichloroacetic acid, difluoroacetic acid, dichloroacetic acid, fluoroacetic acid, chloroacetic acid, and mixtures thereof.

13. The process as claimed in claim 1, wherein the carboxylic acid is present in an amount of from 1 to 20 volumes relative to the compound of formula II.

14. The process as claimed in claim 1, wherein the water is present in an amount ranging from 2% to 50% by weight relative to the combined weight of the water and the compound of formula II.

15. The process as claimed in claim 1, wherein the reaction is performed at a temperature of from about 30° C. to about 70° C.

16. The process as claimed in claim 1, wherein the compound of formula I is hydromorphone or a salt thereof, the compound of formula II is hydrocodone or a salt thereof, and:
   (i) the carboxylic acid is selected from the group consisting of trifluoroacetic acid, trichloroacetic acid, difluoroacetic acid, dichloroacetic acid, fluoroacetic acid, chloroacetic acid, and mixtures thereof;
   (ii) the sulfonic acid is selected from the group consisting of methane sulfonic acid, trifluoromethane sulfonic acid, toluenesulfonic acid, and mixtures thereof; and
   (ii) the sulfide compound is selected from the group consisting of dioctyl sulfide, dibutyl sulfide, dipropyl sulfide, diethyl sulfide, dimethyl sulfide, dodecyl methyl sulfide and mixtures thereof.

17. The process as claimed in claim 2, wherein the compound of formula II is hydrocodone or a salt thereof and wherein the process further comprises a preceding step of converting codeine to the hydrocodone.

18. The process as claimed in claim 1, wherein the compound of formula II is formed by a process comprising reacting a compound of formula VII,

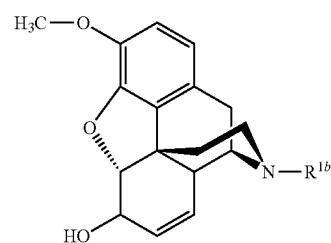

VII wherein $R^{1b}$ is defined according to $R^{1a}$,
with a rhodium complex in an aqueous solvent system; and
optionally the compound of formula VII and the rhodium complex are mixed together with an organic additive selected from the group consisting of acetone, isopropanol, tert-butanol and mixtures thereof.

19. The process as claimed in claim 18, wherein the rhodium complex is prepared from a [Rh(COD)(CH₃CN)₂](BF₄) and a phosphine derivative, wherein the COD is 1,5-cyclooctadiene.

20. A process for forming hydromorphone, wherein the process comprises:
   (i) converting thebaine to hydrocodone; and
   (ii) converting said hydrocodone to hydromorphone according to a process as claimed in claim 1.

21. A process for preparing a salt of a compound of formula I,

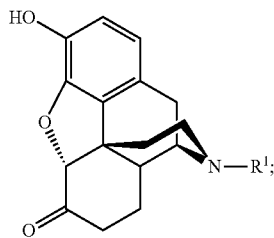

I wherein:

$R^1$ represents hydrogen, $C_{1-12}$ alkyl, $C_{2-12}$ alkenyl, $C_{2-12}$ alkynyl or $C_{3-12}$ cycloalkyl, wherein the alkyl, alkenyl, alkynyl and cycloalkyl are each independently optionally substituted by one or more halogen atoms or phenyl groups;

the process comprises the steps of:
(i) preparing a compound of formula I in accordance with the process defined in claim 1;
(ii) optionally isolating and/or purifying the compound of formula I obtained from the process;
(iii) bringing into association the compound of formula I formed from step (i) or (ii) with an acid; and
(iv) optionally converting the product from step (iii) into a different salt.

22. A process for preparing a pharmaceutical formulation comprising a compound of formula I,

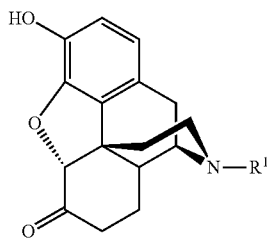

I or a pharmaceutically acceptable salt thereof;
wherein:

$R^1$ represents hydrogen, $C_{1-12}$ alkyl, $C_{2-12}$ alkenyl, $C_{2-12}$ alkynyl or $C_{3-12}$ cycloalkyl, wherein the alkyl, alkenyl, alkynyl and cycloalkyl are each independently optionally substituted by one or more halogen atoms or phenyl groups;

the process comprises the steps of:
(i) preparing a compound of formula I or a salt thereof in accordance with a process as defined in claim 1;
(ii) optionally isolating and/or purifying the compound of formula I or a salt thereof obtained from the process; and
(iii) bringing into association the compound of formula I or a salt thereof formed from step (i) or (ii) with one or more pharmaceutically-acceptable excipients, adjuvants, diluents or carriers.

23. A process for preparing a prodrug of a compound of formula I,

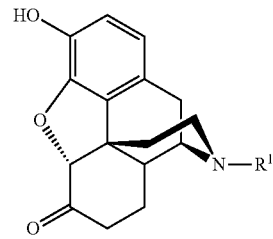

I or a pharmaceutically acceptable salt thereof;
wherein:

$R^1$ represents hydrogen, $C_{1-12}$ alkyl, $C_{2-12}$ alkenyl, $C_{2-12}$ alkynyl or $C_{3-12}$ cycloalkyl, wherein the alkyl, alkenyl, alkynyl and cycloalkyl are optionally substituted by one or more halogen atoms or phenyl groups;

the process comprises the steps of:
(i) preparing a compound of formula I in accordance with the process as defined in claim 1;
(ii) optionally isolating and/or purifying the compound of formula I obtained from the process; and
(iii) converting the compound of formula I obtained from step (i) or (ii) into a prodrug of the compound of formula I by reacting with a reagent that is capable to react with a hydroxyl functional group, an enol tautomer, a carboxyl functional group, or an amine group to form the prodrug of the compound of formula I, wherein the product is an ester derivative, a carbamate derivative, an N-acyl derivative, or an N-Mannich base derivative of the compound of formula I.

* * * * *